United States Patent [19]
Turnbull

[11] Patent Number: 5,817,063
[45] Date of Patent: Oct. 6, 1998

[54] FILTERS

[75] Inventor: Christopher Stratton Turnbull, Hythe, England

[73] Assignee: Smiths Industries PLC, London, England

[21] Appl. No.: 903,147

[22] Filed: Jul. 30, 1997

[30] Foreign Application Priority Data

Aug. 20, 1996 [GB] United Kingdom .................... 9617448
Aug. 20, 1996 [GB] United Kingdom .................... 9617449

[51] Int. Cl.[6] ...................................................... A61M 5/30
[52] U.S. Cl. .............................................................. 604/190
[58] Field of Search .................................. 604/190, 187, 604/240, 241, 242, 243

[56] References Cited

U.S. PATENT DOCUMENTS

| 3,822,701 | 7/1974 | Cloyd ................................. 604/243 X |
| 3,906,930 | 9/1975 | Guerra ............................... 604/241 X |
| 3,906,946 | 9/1975 | Nordstrom . | |
| 4,161,177 | 7/1979 | Fuchs . | |
| 4,485,014 | 11/1984 | Gilroy et al. . | |

FOREIGN PATENT DOCUMENTS

| 1221625 | 10/1969 | United Kingdom . |
| 1498249 | 8/1975 | United Kingdom . |
| 2061125 | 5/1981 | United Kingdom . |
| 2110556 | 6/1983 | United Kingdom . |
| 2225950 | 6/1990 | United Kingdom .................... 604/243 |
| 92/18193 | 10/1992 | WIPO . |

*Primary Examiner*—John D. Yasko
*Attorney, Agent, or Firm*—Pollock, Vande Sande & Priddy

[57] ABSTRACT

An epidural filter has a planar housing with a flat lower surface taped to the patient's skin. An outlet at one end of the housing is connected to the epidural catheter and opens onto the lower surface of the filter element. The inlet at the other end of the housing is shaped to receive the nose of a syringe and opens onto the upper surface of the filter element. The inlet is either fixed at an angle of about 30° to the lower surface of the housing, or can be displaced upwardly to such an angle by means of a resilient portion, to facilitate connection to the inlet.

9 Claims, 2 Drawing Sheets

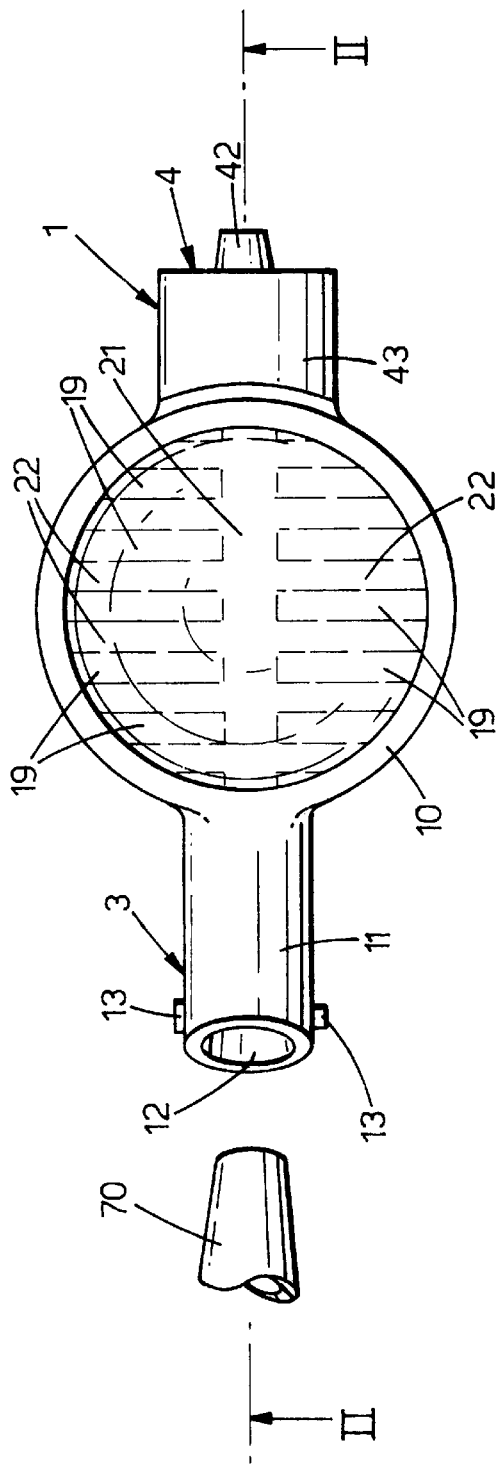
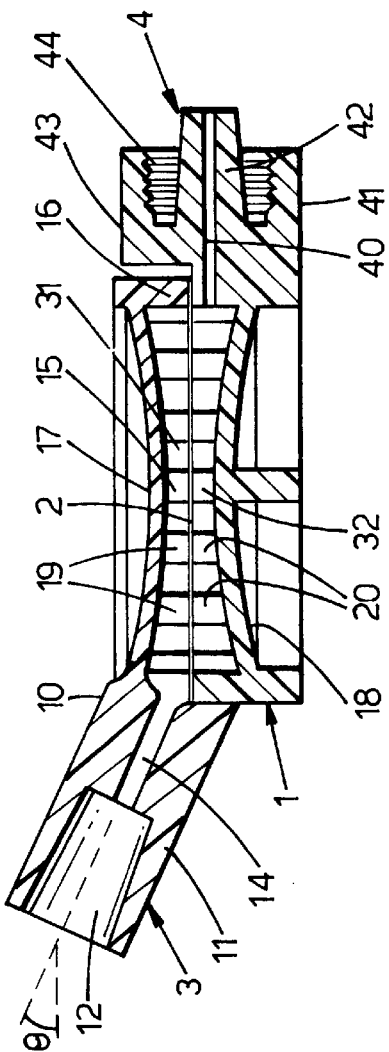

FILTERS

BACKGROUND OF THE INVENTION

This invention relates to filters.

The invention is more particularly concerned with medical filters such as for use in intravenous or epidural applications.

It is usual practice in epidural anaesthesia to connect a filter at the machine end of the epidural catheter. The filter has an inlet to which the nose of a syringe is connected so that anaesthetic fluid injected out of the syringe is filtered before reaching the patient. One of the main purposes of the filter is to remove any particulate matter, such as, for example, shards of glass that might enter the syringe when medication is aspirated from a glass ampoule. The filters are often taped to the patient's skin and, for this reason, they are usually of a flat construction, that is, the plane of the filter element is parallel to the axes of the inlet and outlet, the inlet opening to the upper surface of the filter element and the outlet opening to the lower surface of the filter element. An example of an epidural filter is described in U.S. Pat. No. 4,485,014. In this filter, the inlet is a conventional female luer coupling and the outlet incorporates a connector that makes direct connection with the epidural catheter. More usually, however, the inlet of the filter has a locking luer connection, which engages a cooperating connection on a separate epidural connector. Such a filter is sold by Portex Limited of Flythe, Kent, England. Another flat filter is described in U.S. Pat. No. 4,009,715.

One problem with such filters is that, when the filter is taped to the patient's skin, the inlet lies relatively close to the surface of the skin, making it difficult to connect a syringe to the inlet without first untaping the filter or twisting the filter away from the skin surface.

BRIEF SUMMARY OF THE INVENTION

It is an object of the present invention to provide an improved filter.

According to the present invention there is provided medical filter comprising an outer housing of generally planar shape the lower surface of which is adapted to lie against a support surface, the housing containing a filter element and having an outlet opening onto one surface of the filter element and an inlet opening onto the opposite surface of the filter element, the inlet being located towards one end of the housing and being arranged to be inclined upwardly at an angle to the lower surface of the housing so as to facilitate connection to said inlet.

The angle is preferably about 30°. The inlet may be fixed at the inclined angle or displaceable upwardly to the inclined angle in which case the inlet may have a resilient portion that can be bent to enable the inlet to be inclined upwardly. Preferably, the outlet has a connection for an epidural catheter and the inlet has a connection for a syringe.

Two filters according to the present invention, will now be described, by way of example, with reference to the accompanying drawings.

BRIEF DESCRIPTION OF THE DRAWINGS

FIG. 1 is a plan view of a first filter;

FIG. 2 is a sectional side elevation of the filter of FIG. 1 along the line II—II.

DETAILED DESCRIPTION OF THE PREFERRED EMBODIMENTS

Figure 3:
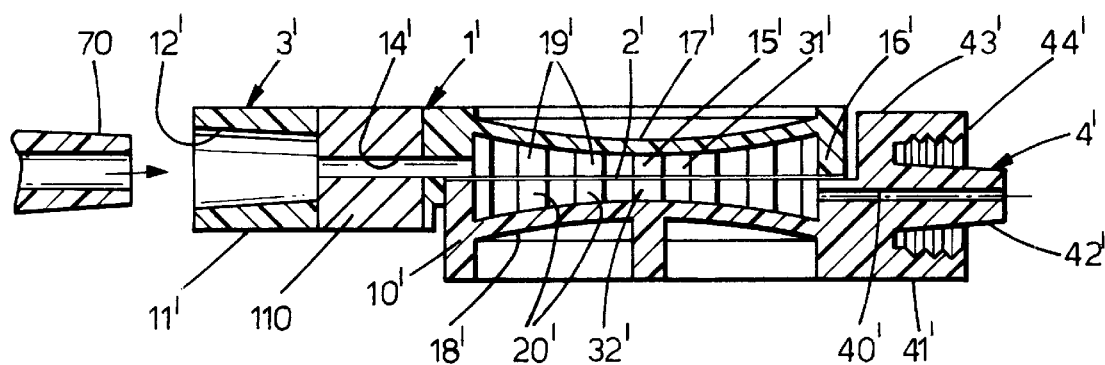
FIG. 3 is a sectional side elevation of an alternative filter.

With reference first to FIGS. 1 and 2, the filter assembly comprises a housing 1, having a filter element 2 located between an inlet 3 and an outlet 4 at opposite ends of the housing. The housing 1 has a rigid body 10 of transparent plastic material and substantially planar, circular shape. The inlet 3 is provided at the rear end of the body 10 by a tubular extension 11 having a female luer-tapered bore 12 and outwardly-extending locking lugs 13. The extension 11 is inclined upwardly away from the lower and upper surfaces of the housing, at an angle θ of about 30°. The bore 12 opens through a smaller diameter passageway 14 into a circular filter chamber 15. The chamber 15 is defined by a cylindrical wall 16 and upper and lower faces 17 and 18 respectively. The outer surface of the upper face 17 provides an unobstructed surface across which a length of adhesive tape can be applied, as described below.

Both faces 17 and 18 have vertical struts 19 and 20 respectively on their inner surfaces, which extend parallel to one another transversely of the housing 1, from the edge to within a short distance of its center, thereby leaving a narrow channel 21. The channel 21 extends at right angles to the struts 19 and 20 longitudinally of the assembly, and communicates with side passages 22 extending at right angles to the channel, to the edge of the filter element 2. The two sets of struts 19 and 20 support the filtering element 2, which is sandwiched between them. The filter element 2 divides the filter chamber 15 into an upper, inlet compartment 31 and a lower, outlet compartment 32. The upper compartment 31 communicates with the inlet opening 3 via the bore 14; the lower compartment 32 communicates with the outlet 4 via a bore 40.

The outlet 4 is provided at the other end of the housing 10, on a tubular forward extension 41. This extension 41 has an inner male luer-tapered nose 42 through which extends the bore 40. An outer collar 43 coaxially encompasses the nose 42 and is provided, on its inner surface, with a screw thread 44. The outlet 4 receives a conventional female luer connection on an epidural connector (not shown).

In use, an epidural catheter is connected to the outlet 4 of the filter using a conventional connector. Anaesthetic fluid is administered by inserting the nose 70 of a syringe in the inlet 3 of the filter. The filter element 2 ensures that no bacteria or particulate matter passes from the syringe to the epidural catheter. The filter is then fastened to a convenient support surface, such as the skin of the patient, by a length of adhesive tape placed laterally across the filter, so that it adheres to the upper surface of the filter and to the skin on opposite sides of the filter. When additional doses of medication need to be administered by syringe, this can be accomplished readily without the need to remove the filter from the skin or to twist it away from the skin, because the raised angle of the inlet 3 enables the syringe to access the inlet without any obstruction from the skin. Where the filter is attached to some other support surface, such as bedding, a piece of medical equipment or the like, it is also an advantage not to have to untape the filter.

Instead of the filter inlet being fixed at an upwardly inclined angle, it could be displaceable to such an angle in the manner of the filter shown in FIG. 3. Components of the filter shown in FIG. 3 equivalent to those in the filter of FIGS. 1 and 2 are given the same reference number with a prime '. The filter shown in FIG. 3 is identical with that of FIGS. 1 and 2 except in the construction of the inlet 3'. In this case, the natural position of the inlet 3' is extending parallel to the plane of the housing 10' and the filter element 2'. The tubular extension 11' forming the inlet 3' has an intermediate portion 110 along its length formed from a resilient, flexible material, such as PVC. The resilient portion 110 extends from the forward end of the bore 12' to a location just before the forward end of the extension 11'. The intermediate portion 110 enables the inlet 3' to be bent up at an angle relative to the upper surface of the housing 10' for connection to a syringe or the like. The resilient nature of the intermediate portion ensures that the inlet 3' returns to a flat position after use, thereby presenting the minimum obstruction.

There are various ways in which the filter shown in FIG. 3 could be made. For example, the resilient, intermediate portion could be moulded separately from the rigid parts of the housing and subsequently joined between the main part of the housing and the rear part of the inlet. Another, preferred method, however, is to mould the resilient portion directly onto rigid parts of the housing using a two-shot moulding process in a common mould. In this, the rigid parts are moulded first by injecting a high-temperature melting point plastics into cavities defining the main part of the housing and the rear end of the inlet. At this stage, the cavity defining the intermediate part 110 of the extension 11' is blocked with a movable die. After the high-temperature plastics has been injected and solidified, the movable die is removed and a lower-temperature, resilient plastics material is injected into the cavity defining the intermediate portion 110 of the tubular extension. This second material bonds onto the first material to form a secure joint between them. The advantage of this method is that there is no need for any assembly steps to join the resilient part to the non-resilient part.

At the same time as moulding the resilient part of the inlet, it would be possible to mould a resilient pad of the same material onto the lower surface of the housing so as to form a softer surface for contacting the patient.

An inlet with an adjustable angle need not be provided by a flexible portion of the inlet but it could be formed by a swivel coupling between the inlet and the main part of the housing. The swivel coupling could be provided by moulding the inlet as a separate component with a swivel joint at one end and then connecting the swivel joint in a cooperating socket or the like on the main part of the housing. Alternatively, the swivel joint could be formed by moulding into the socket from a plastics of a different melting point from the main part of the housing.

It will be appreciated that the present invention is not confined to epidural filters but could be used with other medical filters, such as, for example, for use with intravenous catheters.

What I claim is:

1. A medical filter comprising: an outer housing of generally planar shape, said housing having a lower surface adapted to lie against a surface of a patient's body; a filter element located in said housing; an outlet opening onto one surface of said filter element; and an inlet, said inlet having a first end and a second end, said inlet extending as a straight line between said first and second ends, said first end opening onto an opposite surface of said filter element towards one end of said housing, said inlet having a coupling aligned at said second end, and said inlet being arranged to be inclined upwardly at an angle to the lower surface of the housing such that connection can be made to said coupling at an angle to the surface of the patient's body.

2. A filter according to claim 1, wherein said angle is about 30°.

3. A filter according to claim 1, wherein said inlet is fixed at said angle.

4. A filter according to claim 1, wherein said inlet is displaceable upwardly to said angle.

5. A filter according to claim 4, wherein said inlet has a resilient portion that can be bent to enable said inlet to be inclined upwardly.

6. A filter according to claim 1, wherein said outlet has a connection for an epidural catheter.

7. A filter according to claim 1, wherein said inlet has a connection for a syringe.

8. An epidural filter comprising: an outer housing of generally planar shape, said housing having a lower surface adapted to lie against a surface of a patient's body; a planar filter element located in said housing; an outlet opening onto a lower surface of said filter element, said outlet being adapted for connection to an epidural catheter; and an inlet, said inlet having a first end and a second end, said inlet extending as a straight line between said first and second ends, said first end opening onto an upper surface of said filter element towards one end of said housing, said inlet having a coupling aligned at said second end adapted for connection to a syringe, and said inlet being inclined upwardly at an angle to said lower surface of the housing such that connection can be made to said coupling by the syringe inclined at an angle to said surface of the patient's body.

9. An epidural filter comprising: an outer housing of generally planar shape, said housing having a lower surface adapted to lie against a support surface; a planar filter element located in said housing; an outlet opening onto a lower surface of said filter element, said outlet being adapted for connection to an epidural catheter; and an inlet opening onto an upper surface of said filter element, said inlet being adapted for connection to a syringe, said inlet being located towards one end of said housing and being displaceable upwardly from a first position where it extends parallel to the lower surface of the housing to a second position where it is inclined upwardly at an angle to the lower surface of said housing to facilitate connection of said syringe to said inlet.

* * * * *